United States Patent [19]
Boom

[11] Patent Number: 5,710,496
[45] Date of Patent: Jan. 20, 1998

[54] DRIVE INCLUDING PID POSITION FEEDBACK DRIVE AND CONTROL SYSTEM FED BY SPEED CONTROL UNIT AND X-RAY DEVICE COMPRISING SUCH A DRIVE

[75] Inventor: Marcel A.G. Boom, Eindhoven, Netherlands

[73] Assignee: U.S. Philips Corporation, New York, N.Y.

[21] Appl. No.: 521,187

[22] Filed: Aug. 30, 1995

[30] Foreign Application Priority Data

Sep. 1, 1994 [EP] European Pat. Off. ............. 94202500

[51] Int. Cl.[6] ...................................... H02B 7/00
[52] U.S. Cl. .............................. 318/610; 318/653
[58] Field of Search ....................... 318/609, 610, 318/652, 653, 661, 254, 439, 138; 364/565, 566; 373/93, 94

[56] References Cited

U.S. PATENT DOCUMENTS

| | | |
|---|---|---|
| 4,639,884 | 1/1987 | Sagues ............................ 364/565 |
| 4,642,542 | 2/1987 | McKeand ........................ 318/636 |
| 4,716,535 | 12/1987 | Yoshida et al. ................. 364/565 |
| 4,999,557 | 3/1991 | Inoue .............................. 318/609 |
| 5,059,880 | 10/1991 | Hiroi ............................... 318/610 |
| 5,130,710 | 7/1992 | Salazar .............................. 341/11 |
| 5,237,521 | 8/1993 | Raj et al. ..................... 364/565 X |
| 5,248,921 | 9/1993 | Kato et al. ................... 318/610 X |
| 5,287,396 | 2/1994 | Stegehuis ........................ 378/98.2 |

*Primary Examiner*—Jonathan Wysocki
*Attorney, Agent, or Firm*—Jack D. Slobod

[57] ABSTRACT

A motor drive having a very large dynamic speed range comprises a PID position feedback control system (8) in which the motor position is readjusted on the basis of the difference between the instantaneous ($x_a$) and the nominal ($x_s$) position. A series of nominal positions ($x_s$) is determined from a nominal speed (v) in a speed control unit (5). The successive nominal positions ($x_s(t)$) in a series exhibit a constant difference ($\Delta x$) relative to one another and are presented to the PID position feedback control system (8) with fixed intervals ($\Delta t$). A drive of this kind is used, for example in the beam collimator of an X-ray device.

20 Claims, 1 Drawing Sheet

DRIVE INCLUDING PID POSITION FEEDBACK DRIVE AND CONTROL SYSTEM FED BY SPEED CONTROL UNIT AND X-RAY DEVICE COMPRISING SUCH A DRIVE

BACKGROUND OF THE INVENTION

1. Field of Invention

The invention relates to a drive, comprising a motor with a motor shaft, a feedback control system for positioning the motor shaft in a nominal position, and an input for entering the nominal position. The invention also relates to an X-ray device, comprising an X-ray source and an adjustable diaphragm, or a collimator, with a displaceable shutter arranged in front thereof.

2. Description of the Related Art

A drive of this kind is known from Patents Abstracts of Japan, Kokai No. JP-A 5-11850. The cited publication describes an electric control system in which the differential control cycle is varied by means of switches in dependence on the speed, thus enabling smooth movement at a very low speed.

For a number of applications it is necessary to control the speed at which the displacement takes place. When very large differences in speed are necessary, a gear box is used for this purpose. For the displacement of lead shutters in a beam collimator in an X-ray device, a dynamic range of a factor 3000 is required so as to execute a small variation of the setting sufficiently accurately and smoothly and to execute a large variation within a very short period of time. In the known drive a gear box will be necessary. A gear box has the drawback of a comparatively large mass to be moved and it also requires a considerable amount of space. A mechanical system of this kind also has the drawback of play and inaccuracy of positioning when the gear ratio is changed, and it also requires additional maintenance.

SUMMARY OF THE INVENTION

It is inter alia an object of the invention to provide a drive whereby a very large dynamic range of more than approximately a factor 1000 can be realized without utilizing a gear box.

To this end, a drive in accordance with the invention is characterized in that said input is coupled to a speed control unit which is arranged to supply the feedback control system with a series of nominal positions which are presented with substantially equal time intervals, the differences between successively presented nominal positions having substantially the same values. Slow movement of the motor shaft is achieved by such intermittent entering of each time a new nominal position which exhibits each time a small difference relative to the preceding nominal position. The motor shaft can be displaced over a large range at a high speed when a large difference is entered. The speed of the motor can be controlled by changing the difference between two successive nominal positions and by changing the time interval.

In order to enable very slow movement, the drive in accordance with the invention is characterized in that the speed control unit is arranged to present two successive nominal positions, from a series of positions presented, with a time interval which is approximately equal to the time required by the drive so as to position the motor shaft in the nominal position. When the motor does not come to a standstill before the next nominal position is entered, smooth movement is also possible in the case of low speeds. The lowest possible or minimum non-zero smooth speed is then determined by the minimum difference between two successive nominal positions in response whereto motor movement still takes place.

A further embodiment of the drive in accordance with the invention is characterized in that the feedback control system is a proportional-integral-differential (PID) control system. Such a control system is a standard system whose properties are well known.

The drive in accordance with the invention is preferably characterized in that the feedback control system is a digital control system. In the case of analog position control, the maximum value of the drive signal limits the number of revolutions of the motor. In the case of digital control, this limitation can be eliminated by using a drive signal which is modulo an integer number of revolutions, so that the number of revolutions of the motor is not limited.

A drive in accordance with the invention is preferably characterized in that the feedback control system comprises an incremental encoder. The use of an incremental encoder, for example an optical encoder, is advantageous because such an encoder is very accurate and its range is not limited.

The drive in accordance with the invention can be advantageously used for the displacement of the shutters in a collimator of an X-ray device.

BRIEF DESCRIPTION OF THE DRAWING

These and other, more detailed aspects of the invention will be described in detail hereinafter, by way of example, with reference to the drawing, wherein.

DETAILED DESCRIPTION OF THE PREFERRED EMBODIMENT

Figure 1:
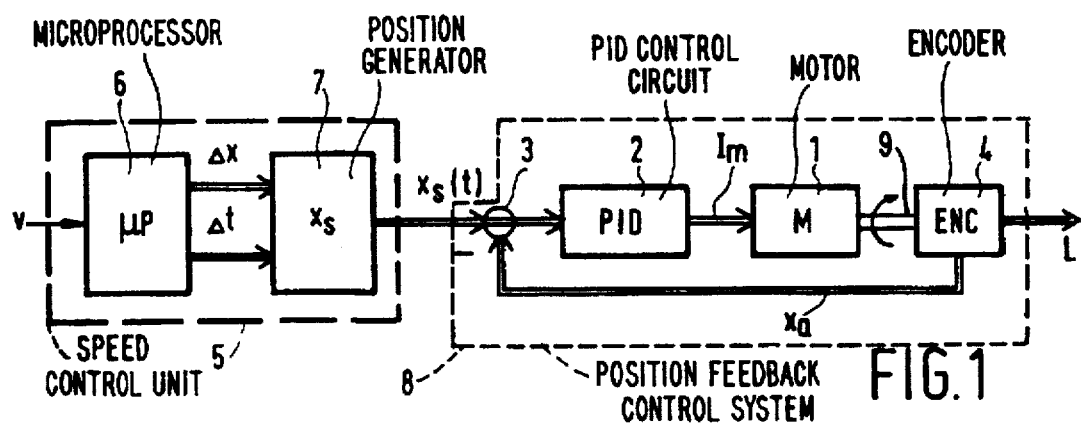
FIG. 1 shows diagrammatically a drive in accordance with the invention.

FIG. 1 shows diagrammatically a drive in accordance with the invention comprising a position feedback control system 8 which receives a position command signal $X_s$ (t) from a speed control unit 5. Position feedback control system 8 comprises: a motor 1, which may be a DC motor or an AC motor, for driving a load L is energized by a motor current $I_m$ originating from a proportional-integral-differential control circuit 2. In the PID control circuit the value of the motor current $I_m$ is determined on the basis of an input signal which is proportional to the difference between the instantaneous position $x_a$ of the motor 9 and a nominal position $x_s$. The difference between the signals representing $x_a$ and $x_s$ is determined in a differencing circuit 3. The instantaneous position of the motor shaft 9 is measured, for example by means of a rotating encoder 4 mounted on the motor shaft. The position measurement can be performed not only on the motor shaft 9 but also by measuring the displacement of the load L.

The speed of the motor shaft 9 is controlled by determining in speed control unit 5 a position command signal $x_s$ (t) in the form of a series of nominal positions presented to the position command input 10 of differencing circuit 3 at different instants t, corresponding to a nominal speed indicated by a speed command signal v supplied to the speed control unit 5. From the nominal speed indicated by speed control signal v, an increment Δx and a time interval Δt are determined in the speed control unit 5, for example in a microprocessor 6. These two values are subsequently converted, for example in the position generator 7 to produce the position command signal $x_r(t)$ in the form of series of nominal positions; which exhibit a constant difference Δx relative to each other and which are successively applied to the position command input 10 of the differencing circuit 3 with a fixed time interval Δt. Thus, a displacement with a mean speed Δx/Δt (=v) is obtained. The maximum value of the speed is determined by the maximum motor speed, the minimum speed which is still smooth by the inertia of the motor with the load, the resolution of the encoder, and the smallest possible value of Δx at which displacement still occurs. In the case of a digital system, if desired, a larger number of different mean speeds can be realized by varying the values of Δx and/or Δt instead of keeping them constant. When the nominal speed v is changed, the value of Δx and/or Δt will be changed by the microprocessor 6.

For a slow but smooth movement preferably as small as possible values of Δx are used and Δt is varied so as to obtain the desired speed. For high speeds Δx as well as Δt can be varied. By utilizing a high-resolution rotary encoder a speed of less than one revolution per minute can be realized for a motor whose maximum speed amounts to some 8000 revolutions per minute. 0.3 revolutions per minute is possible when use is made of an encoder with 1500 lines per revolution.

Figure 2:
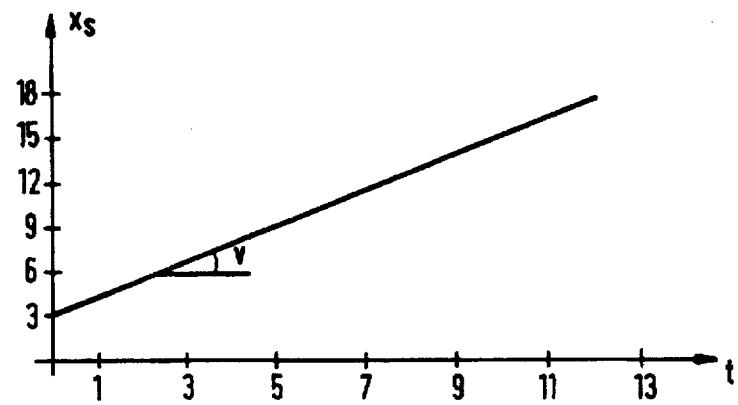
FIG. 2 shows the nominal position as a function of time in an analog feedback system.

FIG. 2 shows the relation between the nominal position $x_r$ and the time t for an analog control system. The speed is represented by the slope of the line 10. In an analog control system the nominal position $x_r$ is given by an electric voltage and is limited in that the voltage cannot increase indefinitely. When this voltage reaches its maximum value, the motor stops. Therefore, preferably a digital control system is used in which the nominal position can be entered modulo an integer number of revolutions of the encoder 4.

Figure 3:
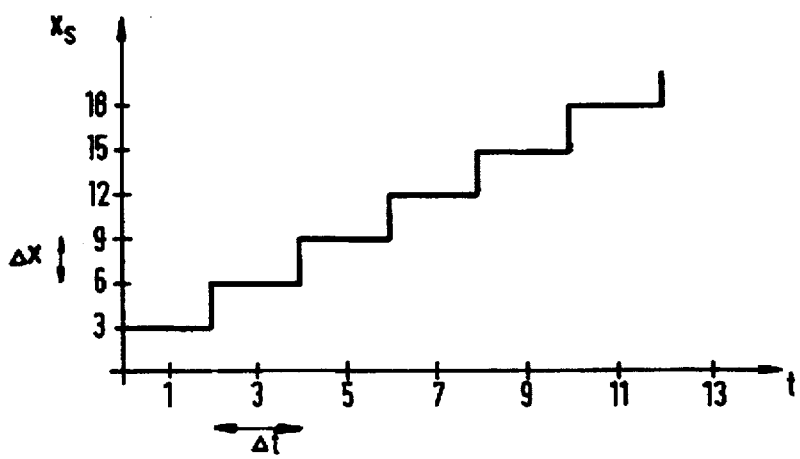
FIG. 3 shows a nominal position as a function of time in a digital feedback system.

FIG. 3 shows the nominal position $x_r$ as a function of time t for a digital system. Therein, time can be represented as a number of clock pulses of a duration of, for example 5 ms each and a position can be represented as a number of encoder increments, one revolution corresponding to from 1000 to 2000 increments for a typical encoder. An increase of the number of increments between two nominal positions means an increase of the speed; an increase of the number of clock pulses in a time interval means a decrease of the speed.

A drive in accordance with the invention can be advantageously used when a combination of accurate positioning and a large dynamic speed range is desirable. This is the case, for example for plotters, wafer steppers, mounting machines for electronic components, etc. A specific application in an X-ray device is shown in FIG. 4.

Figure 4:
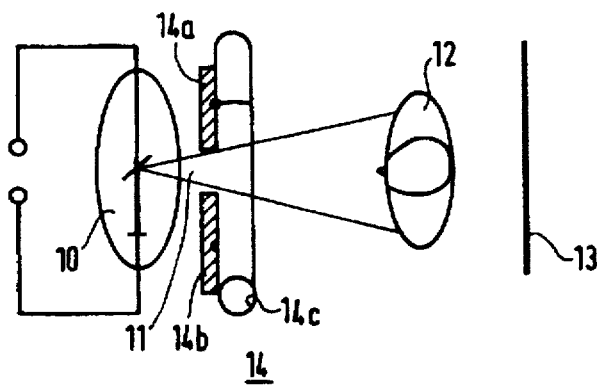
FIG. 4 shows an X-ray device in accordance with the invention.

FIG. 4 shows an X-ray source 10 which generates an X-ray beam 11. The X-ray beam 11 forms a shadow image of a patient 12 on an X-ray detector 13, for example a photographic plate, the entrance screen of an image intensifier, or a semiconductor detector. During the formation of X-ray images it is necessary to adapt the cross-section of the beam 11 to the image to be formed and the remaining X-rays must be stopped, for example in order to shield parts of the patient or to prevent local overexposure of the detector 13. Shielding is effected by means of a collimator 14 which is arranged near the X-ray source 10 and which comprises a number of displaceable lead shutters 14a and 14b which can be displaced by means of a motor 14c. Accurate shutter adjustment requires slow and controlled driving of the shutters because of the multiplication factor which results from the difference in distance from collimator 14 and patient 11 to the X-ray source 10. One possible motor speed is 2.5 revolutions per minute. On the other hand, for example when a new format for an exposure is adjusted, the displacement of the shutters to a standard setting may not be more time-consuming than the adjustment of the other parts of the X-ray apparatus. This requires a motor speed of some 8000 revolutions per minute.

I claim:

1. A drive, comprising:

a motor with a motor shaft;

a feedback control system for positioning the motor shaft in a nominal position represented by a position command signal, and an input for receiving the position command signal, and a speed control unit having an input for receiving a velocity command, said speed control unit being arranged to produce the position command signal in response to the velocity command such that the position command signal represents a series of nominal positions which are presented with differences (Δx) between successively presented nominal positions having substantially a same value, and time intervals (Δt) between successively presented nominal positions having substantially a same value, by at least calculating the value of the time intervals (Δt) such that the value of the time intervals (Δt) is changed in response to a change in the velocity control signal, and to supply the position command signal to the input of the feedback control system.

2. A drive as claimed in claim 1, wherein the speed control unit is arranged to present the position command signal such that the value of the differences (Δx) between the successively presented nominal positions is substantially equal to the smallest possible value at which displacement of the motor shaft occurs at a smooth speed.

3. A drive as claimed in claim 1, wherein the feedback control system is a proportional-integral-differential (PID) control system.

4. A drive as claimed in claim 1, wherein the feedback control system is a digital control system.

5. A drive as claimed in claim 1, wherein the feedback control system comprises an incremental encoder.

6. An X-ray device, comprising an X-ray source and a displaceable shutter which is arranged in front thereof which is driven by a drive comprising:

a motor with a motor shaft;

a feedback control system for positioning the motor shaft in a nominal position represented by a position command signal, and an input for receiving the position command signal, and a speed control unit having an input for receiving a velocity command, said speed control unit being arranged to produce the position command signal in response to the velocity command such that the position command signal represents a series of nominal positions which are presented with differences (Δx) between successively presented nominal positions having substantially a same value, and time intervals (Δt) between successively presented nominal positions having substantially a same value, by at least calculating the value of the time intervals (Δt) such that the value of the time intervals (Δt) is changed in response to a change in the velocity control signal, and to supply the position command signal to the input of the feedback control system.

7. A drive as claimed in claim 2, wherein the feedback control system is a proportional-integral-differential (PID) control system.

8. A drive as claimed in claim 2, wherein the feedback control system is a digital control system.

9. A drive as claimed in claim 3, wherein the feedback control system is a digital control system.

10. A drive as claimed in claim 7, wherein the feedback control system is a digital control system.

11. A drive as claimed in claim 2, wherein the feedback control system comprises an incremental encoder.

12. A drive as claimed in claim 3, wherein the feedback control system comprises an incremental encoder.

13. A drive as claimed in claim 4, wherein the feedback control system comprises an incremental encoder.

14. A drive as claimed in claim 8, wherein the feedback control system comprises an incremental encoder.

15. A drive as claimed in claim 9, wherein the feedback control system comprises an incremental encoder.

16. A drive as claimed in claim 10, wherein the feedback control system comprises an incremental encoder.

17. An X-ray device as claimed in claim 6, wherein the speed control unit is arranged to present the position command signal such that the value of the differences ($\Delta x$) between the successively presented nominal positions is substantially equal to the smallest possible value at which displacement of the motor shaft occurs at a smooth speed.

18. An X-ray device as claimed in claim 6, wherein the feedback control system is a proportional-integral-differential (PID) control system.

19. An X-ray device as claimed in claim 17, wherein the feedback control system is a proportional-integral-differential (PID) control system.

20. An X-ray device as claimed in claim 19, wherein the feedback control system is a digital control system.

* * * * *